United States Patent [19]

Fox et al.

[11] 4,384,143

[45] May 17, 1983

[54] PROCESS FOR PREPARING PURIFIED BIS(3,5-DIALKYL-4-HYDROXYPHENYL) SULFONE

[75] Inventors: Daniel W. Fox, Pittsfield; Edward N. Peters, Lenox, both of Mass.

[73] Assignee: General Electric Company, Pittsfield, Mass.

[21] Appl. No.: 259,523

[22] Filed: May 1, 1981

[51] Int. Cl.³ ............................................ C07C 147/10
[52] U.S. Cl. ...................................... 568/33; 528/171
[58] Field of Search ........................................... 568/33

[56] References Cited

U.S. PATENT DOCUMENTS 3,277,183 10/1966 Heller et al. ......................... 568/33
3,383,421 5/1968 Fox et al. ............................. 568/33
3,737,409 6/1973 Fox ..................................... 528/171

Primary Examiner—Donald G. Daus
Assistant Examiner—M. C. Eakin
Attorney, Agent, or Firm—Hedman, Casella, Gibson, Costigan & Hoare

[57] ABSTRACT

Purified bis(3,5-dialkyl-4-hydroxyphenyl) sulfone useful for production of improved carbonate polymer is described. This sulfone is precipitated by deammoniation of an aqueous solution and then removed from the supernatant solution. This produces a product having minimal phenol sulfonic impurities. It may be employed to form carbonate polymer having improved physical properties.

5 Claims, No Drawings

PROCESS FOR PREPARING PURIFIED BIS(3,5-DIALKYL-4-HYDROXYPHENYL) SULFONE

BACKGROUND OF THE INVENTION

The production of sulfones through reaction of 2,6-dialkyl phenol with a sulfonating agent is known. The product, however, generally suffers from low purity. Consequently, various steps have been employed to reduce contamination.

In, for example, U.S. Pat. No. 3,383,421 of Fox et al, there is claimed a process yielding bis(3,5-dialkyl-4-hydroxyphenyl) sulfone. That process involves:

(a) reaction of a 2,6-dialkyl phenol where each alkyl group has from 1 to 4 carbon atoms with sulfuric acid within a temperature range of 155° to 170° C. in the presence of an organic liquid capable of forming an azeotrope with the water of reaction, the azeotrope having a boiling point within the reaction temperature range;

(b) recovering sulfone from the reaction mixture;

(c) dissolving said sulfone in aqueous solution of caustic soda or ammonia;

(d) neutralizing the aqueous solution with acid to pH ranging between 4 and 6; and (e) collecting the sulfone in the form of white crystals.

The disclosure of that patent emphasized the importance of steps (c) and (d) to product purity. In addition, however, additional measures intended to reduce formation of, or remove, contaminants are mentioned.

The presence of contaminant impurities in bis (3,5-dialkyl-4-hydroxyphenyl) sulfones raises special concerns. They include partial reaction products such as phenol sulfonic acids and by-products of reaction such as quinone type color bodies, sulfonic acid and derivatives and sulfonic isomers.

Impurities are most particularly objectionable for the recent newer usages of bis(3,5-dialkyl-4-hydroxyphenyl) sulfones as monomeric constituents. A representative such usage is described in U.S. Pat. No. 3,737,409 of Fox. There, such sulfones are employed in the production of carbonate polymers.

Whereas these impurities were often tolerable for such prior art utilities as plasticizers, wetting agents, agents for combating pests, auxiliary substances for use in canning, dyestuff and the like, they are very detrimental in the formation of high molecular weight polymers and copolymers. There they may additionally cause undesirable chain termination, branching and cross-linking as well as predispose the product to various degradation processes.

As a result of the foregoing drawbacks diphenyl sulfones of improved purity remain highly desirable.

INTRODUCTION TO THE INVENTION

The present invention involves an improved process for purifying crude bis(3,5-dialkyl-4-hydroyphenyl) sulfone. That process involves:

(a) forming a solution of the crude bis(3,5-dialkyl-4-hydroyphenyl) sulfone in aqueous ammonium hydroxide;

(b) heating the solution to vaporize ammonia and effect selective precipitation of said sulfone; and (c) removing the solid diphenyl sulfone from supernatant solution.

This process results in the production of high purity bis(3,5-dialkyl-4-hydroxyphenyl) sulfone. Most particularly, product having a phenol sulfonic intermediate content of less than 50 ppm is readily obtained. This high purity product is particularly desirable for use in the production of carbonate polymers. There it minimizes side-reactions and results in polymer having an improved melt stability.

DESCRIPTION OF THE INVENTION

The present purification process can be practiced on any crude bis(3,5-dialkyl-4-4-hydroxyphenyl) sulfone. These sulfones are formed from 2,6-dialkyl phenols and have the formula:

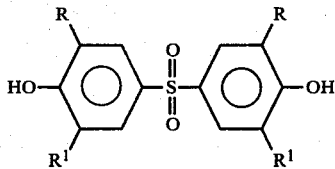

wherein R and R$^1$ are each alkyl groups, most preferably having from 1 to 4 carbons.

The most preferred sulfone in accordance with the present invention is bis(3,5-dimethyl-4-hydroxyphenyl) sulfone formed from 2,6-xylenol.

Crude diphenyl sulfone may, as previously indicated, contain a variety of contaminant impurities. It has been discovered that one of the most deleterious of these impurities is the corresponding phenol sulfonic acid (or salts thereof) reaction intermediate. Even product produced in accordance with such advanced processes as that described in the above-mentioned U.S. Pat. No. 3,383,421 commonly contain in excess of about 500, usually from about 500 to 10,000, parts per million of this intermediate of diphenyl sulfones.

These phenol sulfonic intermediates of bis(3,5-dialkyl-4-hydroxyphenyl) sulfones have further been discovered to be responsible for various drawbacks of carbonate polymers produced from the sulfones. The intermediate interferes with conventional carbonate polymerization and causes melt instability in the resultant polymer or copolymer.

To purify the crude diphenyl sulfone in accordance with the present invention, it must first be solubilized in aqueous ammonium hydroxide. Ordinarily concentrated ammonium hydroxide is employed to dissolve the crude sulfone. Where desired, however, solution containing from about 30 to 15% ammonia by weight of water may be utilized.

The amount of aqueous ammonium solvent may also vary widely. Solutions containing as much as about 30% by weight of crude sulfone have been employed. Ordinarily, however, more dilute solutions provide superior results. Consequently, from about 10 to 20% sulfone (or 80 to 90% solvent) by weight is preferred.

After the sulfone has been solubilized, some particulates may remain. In such event, it is preferred to filter the solution or otherwise remove these additional impurities prior to deammoniation.

In a preferred embodiment, the solution may also contain liquid in addition to the aqueous-ammonium solvent. This liquid should be miscible with water as well as being a selective or preferential solvent for impurities. It is more preferably a liquid in which bis(3,5-dialkyl-4-hydroxyphenyl) sulfone is essentially insoluble. Such a liquid, of which alcohols are representative, aids in insuring optimum purification.

A further optional step in accordance with the present invention involves liquid extraction of the solution. A water immiscible liquid, such as methylene chloride, which is a selective or preferential solvent for impurities may be utilized in a liquid-liquid extraction of the bis(3,5-dialkyl-4-hydroxyphenyl) sulfone containing solution. Again, this embodiment increases the efficiency of purification and a liquid in which the sulfone is essentially insoluble is particularly preferred.

The chief purification step is commenced by heating the solution of crude sulfone to vaporize ammonia. A temperature of at least about 50° C., ordinarily about 50° to 99° C., is usually utilized for this purpose. Where desired, however, a vacuum may be applied to permit lower temperatures.

As the ammonia is removed from the solution, the bis(3,5-dialkyl-4-hydroxyphenyl) sulfone becomes insoluble. Most contaminants—including phenol sulfonic intermediate—remain soluble in the solution. The solid diphenyl sulfone is therefore selectively precipitated and may then be removed from the supernatant solution to effect purification.

After precipitation from the solution, the solid sulfone is preferably washed. This washing helps to remove adherent solution. Any wash medium miscible with the solution and in which the sulfone is insoluble may be employed. Representative media are alcohol, alcohol-water and, preferably, water.

The solid white bis(3,5-dialkyl-4-hydroxyphenyl) sulfone obtained pursuant to the foregoing process is highly pure. Most importantly, product having less than about 50, preferably less than about 30, parts per million of phenol sulfonic impurity is readily obtained. Such product purity is of particular importance in the subsequent production of carbonate polymer. It both reduces conflicting side-reactions incident to polymerization and imparts improved polymer properties.

The bis(3,5-dialkyl-4-hydroxyphenyl) sulfones of the present invention may be converted directly into carbonate polymer by reaction with a carbonate precursor, such as phosgene or the like, in accordance with known technique. Most commonly, however, the sulfone is copolymerized with a bisphenol, especially 2,2-bis (4-hydroyphenyl) propane, as described for example in U.S. Pat. No. 3,737,409 of Fox. The resultant copolymer, in which the sulfone monomer is ordinarily from about 50 to 99% by weight of bisphenol monomer, has been found to be particularly desirable.

These polycarbonates derived from purified bis(3,5-dialkyl-4-hydroxyphenyl) sulfone possess superior physical properties. Most particularly, they avoid the drawback of melt instability now attributed to such sulfone contaminants such as the phenyl sulfonic impurities. This greatly facilitates their use in, for example, their customary applications as textile fibers, packaging films and the like.

The following examples are given by way of illustration only and are not intended as a limitation on the scope of this invention. Many variations are possible without departing from its spirit and scope. Unless otherwise specified herein, all proportions are provided on a weight basis.

EXAMPLE I 200 grams of crude bis(3,5-dialkyl-4-hydroxyphenyl) sulfone, a lavender colored material containing 1.8 wt. % phenol sulfonic intermediate is dissolved in 800 ml concentrated ammonium hydroxide at ambient temperature. The solution is then deammoniated by heating. There is a rapid evolution of ammonia between 48°-50° C. and the sulfone precipitates out of solution. After 5-10 minutes at 50°-60° C. the precipitated material is filtered, washed with 500 ml water, and dried. The resultant lightly tan solid (140 grams; 70% recovery) exhibits less than 30 ppm phenol sulfonic impurity.

EXAMPLE II 25 grams of lavender colored bis(3,5-dialkyl-4-hydroxyphenyl) sulfone containing 1.8 weight % phenol sulfonic intermediate is dissolved in 80 ml concentrated ammonium hydroxide and 20 ml water. This solution is extracted with 50 ml methylene chloride. The methylene chloride, which picks up a yellow color, is separated and the aqueous solution is ammoniated at 90° C. for 10 minutes. The precipitated sulfone is filtered, water washed and dried. The resultant white material (17.8 gram; 71% recovery) contains only 38 ppm phenol sulfonic impurity.

EXAMPLE III 25 grams of crude bis(3,5-dimethyl-4-hydroxyphenyl) sulfone containing 1500 ppm phenol sulfonic intermediate is dissolved in 60 ml concentrated ammonium hydroxide and deammoniated at 50° C. for 10 minutes. The precipitated diphenyl sulfone is isolated by filtration, water washed, and dried to give 17.8 grams (71% recovery) with 72 ppm phenol sulfonic acid.

EXAMPLE IV 50 grams of crude bis(3,5-dimethyl-4-hydroxyphenyl) sulfone is dissolved in 300 ml concentrated ammonium hydroxide and deammoniated between 55°-57° C. The precipitated sulfone is isolated by filtration, washed with 200 ml water, slurried in 500 ml of water at 90° C. for 30 minutes, filtered and dried. The resultant material (25 gram; 50% recovery) shows less than 30 ppm phenol sulfonic acid.

EXAMPLE V 25 grams of crude bis(3,5-dimethyl-4-hydroxyphenyl) sulfone containing 1500 ppm phenol sulfonic impurity is dissolved in 90 ml concentrated ammonium hydroxide and then 60 ml water is added. The solution is deammoniated at 90° C. for 10 minutes. The precipitated sulfone is isolated by filtration, water washed, treated with 300 ml water at 90° C. for 30 minutes, filtered and dried. The recovered 17.1 grams (68%) contained 34 ppm phenyl sulfonic acid.

EXAMPLE VI 50 grams of crude bis(3,5-dimethyl-4-hydroxyphenyl) sulfone (beige colored) containing 1000 ppm phenol sulfonic intermediate is dissolved in 150 ml of concentrated ammonium hydroxide and deammoniated at 60° C. for 10 minutes. The precipitated diphenyl sulfone is isolated by filtration, water washed, and dried. This purified material is light tan in color and contains less than 30 ppm phenol sulfonic acid (35 grams; 70% recovery).

EXAMPLE VII 50 grams of crude bis(3,5-dimethyl-4-hydroxyphenyl) sulfone (beige colored) containing 100 ppm phenol sulfonic intermediate is dissolved in a mixture of 50 ml concentrated ammonium hydroxide and 100 ml acetone. The solution is deammoniated at 60° C. for 10 minutes. The precipitated sulfone is isolated by filtration, water washed, and dried. This purified material is white and contained less than 30 ppm phenol sulfonic acid (42 grams; 84%)

EXAMPLE VIII

Samples of polycarbonate are produced in accordance with the process of U.S. Pat. No. 3,737,409 utilizing an approximately 1:1 mole ratio of bisphenol A to bis(3,5-dimethyl-4-hydroxyphenyl) sulfone compositions of varying purities.

The intrinsic viscosities of the resulting polycarbonate samples are measured, and the samples then aged at 300° C. in an oven. After aging for the times indicated below, the samples are removed and their viscosities remeasured. The results are set forth in the Table below:

| Sample of Content of Phenol Sulfonic Acid (ppm) | Aging Time (min) | Loss in Intrinsic Viscosity (dl./g.) |
| --- | --- | --- |
| 500 | 5 | 0.30 |
| 100 | 5 | 0.10 |
| <30 | 5 | 0.01 |
| <30 | 25 | 0.02 |

As reflected by the above data, the stability of the polycarbonates is greatly improved with increasing purity of the diphenyl sulfone monomer employed in polymerization. The stability reflects a corresponding decrease in conflicting side-reactions induced by phenol sulfonic acid during polymerization.

All the foregoing patents and/or publications are incorporated herein by reference. Obviously, other modifications and variations of the present invention are possible in the light of the above teachings. It is, therefore, to be understood that changes may be made in the particular embodiments of the invention described which are within the full intended scope of the invention as defined by the appended claims.

We claim:

1. A process for the purification of crude bis(3,5-dialkyl-4-hydroyphenyl) sulfone, said process consisting essentially of:
   (a) forming a solution of said crude sulfone in concentrated aqueous ammonium hydroxide;
   (b) heating said solution to from about 50° to 90° C. to vaporize ammonia and effect selective precipitation of sulfone; and
   (c) removing the solid bis(3,5-dialkyl-4-hydroxyphenyl) sulfone from the supernatant solution.

2. The process of claim 1, wherein the solid sulfone is washed after removal from supernatant solution.

3. The process of claim 1, wherein prior to heating, the solution of sulfone is extracted with an immiscible liquid having a solvating preference for impurities over bis(3,5-dialkyl-4-hydroxyphenyl) sulfone.

4. The process of claim 1, wherein the solution of sulfone additionally contains miscible liquid having a solvating preference for impurities over bis(3,5-dialkyl-4-hydroxyphenyl) sulfone.

5. The process of claim 1, wherein the sulfone is bis(3,5-dimethyl-4-hydroxyphenyl) sulfone.

* * * * *